United States Patent [19]

Heim et al.

[11] 4,317,453

[45] Mar. 2, 1982

[54] METHOD AND APPARATUS FOR TESTING A PERSON'S BREATH FOR THE DETERMINATION OF ITS ALCOHOL CONTENT

[75] Inventors: Ulrich Heim, Reinfeld; Hans-Friedhelm Kempin, Munich, both of Fed. Rep. of Germany

[73] Assignee: Drägerwerk Aktiengesellschaft, Fed. Rep. of Germany

[21] Appl. No.: 120,548

[22] Filed: Feb. 11, 1980

[30] Foreign Application Priority Data

Feb. 22, 1979 [DE] Fed. Rep. of Germany ....... 2906876

[51] Int. Cl.³ ............................................. A61B 10/00
[52] U.S. Cl. .................................. 128/719; 128/724; 128/730; 422/84; 73/863.01; 73/204
[58] Field of Search ............... 128/719, 724, 725, 730; 73/421.5 R, 204; 422/84, 85

[56] References Cited

U.S. PATENT DOCUMENTS

| | | | |
|---|---|---|---|
| 1,766,148 | 6/1930 | Sawyer | 73/204 |
| 2,016,660 | 10/1935 | Weeks | 73/204 X |
| 3,592,055 | 7/1971 | Dorman | 73/204 X |
| 3,613,665 | 10/1971 | Gorsuch | 128/730 |
| 3,623,364 | 11/1971 | Withrow | 73/204 |
| 3,645,133 | 2/1972 | Simeth et al. | 73/204 |
| 4,090,078 | 5/1978 | Heim | 422/84 X |

FOREIGN PATENT DOCUMENTS 2522932 12/1976 Fed. Rep. of Germany ........ 422/84

Primary Examiner—Robert W. Michell
Assistant Examiner—John C. Hanley
Attorney, Agent, or Firm—McGlew and Tuttle

[57] ABSTRACT

A method for determining the gas content of a person's breathing air, comprises, first determining when the breathing air is at a condition in which best testing results will be effected. This is done by arranging a capacitor in a breathing tube through which the breathing air is directed. The capacitor is first heated to a predetermined temperature and the breathing air is directed over it so as to cool it until it has attained a predetermined temperature change. This temperature change is such that it will take place when the person's breathing air has its desired constituency. When this occurs, the breathing air is then directed into a test chamber in which it is tested to determine the constituency of the breathing air particularly the percentage of alcohol which it contains. A device for testing a person's breath in addition to the tube through which the breath is directed containing the thermal capacitor also contains a test chamber which is connected to the tube with control means which senses the temperature of the capacitor and permits the flow of the gas into the test chamber only after a predetermined temperature drop has taken place.

8 Claims, 3 Drawing Figures

METHOD AND APPARATUS FOR TESTING A PERSON'S BREATH FOR THE DETERMINATION OF ITS ALCOHOL CONTENT

FIELD AND BACKGROUND OF THE INVENTION

This invention relates to methods and devices for detecting constituents of breathing air in general and, in particular, to a new and useful method for determining the most advantageous measuring instant for testing alcohol content in exhaled breath and to an apparatus for carrying out the aforesaid method.

In accordance with one known concept of the mechanism of alcohol transfer from the human body to the breath, a reliable breath alcohol test can only be taken after a volume corresponding at least to the dead space of the person whose breath is to be checked has already exhaled the dead space being that part of the respiratory tract where no gas exchange between blood and breathing air occurs. Moreover, it is necessary to wait long enough for the socalled "deep lung air" (alveolar air) to be present in the exhaled air and for the alcohol concentration consequently having assumed a saturation value.

More recent test results partly contradict this concept. According to such tests, the alcohol concentration in the exhaled air starts rising spontaneously from the start of exhalation. A conclusion can be drawn from these tests that the alcohol concentration in exhaled breath is not only a result of the gas exchange with the blood effected in the lungs but it is quite significantly determined by the alcohol content of other body fluids present in the respiratory passage, i.e., the said dead space.

One known arrangement for the determination of alcohol concentration measures the alcohol in exhaled breath at a point in time fixed by a timing device. This point in time is determined by the lapse of a settable time interval beginning within the exhalation time span. During this time interval, the breath flow rate must not drop below a fixed minimum flow rate, and the flow must always be in the exhalation direction only. If these two conditions are not met, an error detector will signal the invalidity of the test. The set time interval is to assure that the test person has already exhaled the air from his oral cavity and windpipe at the measuring instant, and that the test instrument then measures the alcohol concentration of the breath from the alveoli of the lungs.

The lapse of the set time interval is determined by the time when a minimum breath volume of preferably at least 80% of the entire breath volume has been exhaled. An integrator can time-integrate the breath flow rate during inhalation and exhalation and determine therefrom the lapse of the time interval by the minimum breath volume. This embodiment is supposed to be unaffected by the physical build of the test person, but the method is not error-proof in cases where the test person is uncooperative. A much too small breath capacity can be feigned by intentionally shallow inhalation. The minimum breath volume then establishing itself automatically, e.g., at 80% of the total breath volume, can then stem practically, from the oral cavity and the throat area only for the test. The alveolar air, which is decisive for an accurate test result, is then not picked up fully (See German Offenlengungschrift No. 24 28 352).

In another known test method and in the breath alcohol measuring instrument designed according to this method, both the $CO_2$ content and the alcohol content in the exhaled breath are measured. Starting from the idea that the $CO_2$ content is a measure for the $O_2$-exchange in the lung, a high $CO_2$ content must point to breath from the lung. For the test, the test instrument first measured continuously the $CO_2$ content in the exhaled air in order to switch on the alcohol measuring section after the attainment of the predetermined threshold value of 4.5% $CO_2$ in the embodiment example, in order to then measure the breath alcohol content.

One inaccuracy of this method is inherent in the individual $CO_2$ values which are subject to wide variations. A generally valid threshold value can, therefore, not be fixed. One test person will not reach the threshold at all, while in others, no air from the lungs may be present yet, although the threshold has been exceeded. Furthermore, an instrument to measure the concentrations of two different gases is rather complicated and sensitive (See U.S. Pat. No. 3,830,630).

Another known method and the associated arrangement starts with the premise that the actual alcohol concentration in the breath is detected only, if that portion of the exhaled air which could find its equilibrium with the blood alcohol concentration in the alveoli of the lungs is examined for its alcohol content. Therefore, the reciprocating air from the mouth and throat area and the mixed air must be separated from the alveolar air for test purposes.

The method, and also the associated arrangement solve this problem by means of an infrared measuring instrument which continuously measures the momentary alcohol concentration while the sample is being taken. A threshold comparator determines the time variation of the measured values, which represents the measure of the rate with which the alcohol concentration increases.

A measured value is transmitted for display only if the rate of increase falls below a given threshold. This first condition results from the fact that the percentage of reciprocating air from the mouth and throat area becomes smaller and smaller as the rate of increase drops and the alveolar air only is still found in the measuring chamber of the arrangement when the threshold has fallen below. As another condition for the transmission of the measured value, the flow velocity of the exhaled air, as determined by a flow meter, must have been above a given value during a given time span up to the transmission of the measured value. This second condition makes certain that the test method progresses as intended. The alcohol concentration is measured by a fast responding infrared measuring instrument inserted in the breath flow. A disadvantage of this arrangement is that, because of the high resolution of the measured values as required for the determination of the rate of increase, an expensive infrared measuring instrument is needed. The reliable detection of the percentage of alveolar air is not feasible with simple, inexpensive, but slow alcohol measuring instruments.

The state of the art can generally be divided into the following two categories:

(a) Exhalation of a minimum volume as product flow x time, as intergral over the flow or volumetric; and (b) correlation with the time curve of the gas parameters varying during exhalation, such as temperature, alcohol concentration, or $CO_2$ concentration.

The disadvantage in category (a) is that the minimum volume is not fixed individually for each test person, and new tests are not taken into account which have proven that the level of alcohol concentration reached is not only a function of the exhaled volume, but just as much a function of time. The alcohol figures differ when one and the same volume of air is exhaled intentionally fast or intentionally slow. If the test person holds his breath temporarily before exhaling, a high alcohol figure already results after exhaling a relatively small volume. Another characteristic of category (a) is that the direction of the flow must also be monitored so that it is recognized whether the person inhales fresh air.

A disadvantage of category (b) is that costly equipment, such as an alcohol sensor of high time resolution, or an additional $CO_2$ sensor must be used, or that the correlation as over the temperature cannot be proven reliably.

SUMMARY OF THE INVENTION

The present invention provides a simple and reliable method and an associated arrangement or apparatus for the determination of the correct measuring instant of equipment used for testing the alcohol content in exhaled air, which is suitable for the entire diversity of persons which could possibly be tested and is appropriate for use under all environmental conditions.

The present invention provides a device for determining the alcohol content of a person's breath which comprises a tube through which the person's breath is directed. A body having a certain heat capacity, hereafter referred to as thermal capacitor, is arranged in the tube and means are provided for heating this thermal capacitor to a predetermined temperature. Means are also provided for sensing the temperature of the thermal capacitor and arrangements are made for directing the breathing air into a test chamber when the temperature of the capacitor has been reduced by the breathing air passing over it to the predetermined value. This value is known by experience as the one when the breathing air is best suited for determining the alcohol content in particular.

With the method of the invention, the thermal capacitor includes a heating element which makes it possible to heat the thermal capacitor to a predetermined temperature. Thereafter, the breathing air is directed over the capacitor so as to cool it and when a certain temperature drop has taken place, the breathing air is directed through a connecting passage to a test chamber by operating a valve. This ensures that the breathing air is directed to the test chamber only when its content and characteristic is such that the most accurate testing results will be obtained.

The method, according to the invention, utilizes, in an advantageous manner, the new knowledge that the alcohol concentration in exhaled air is composed of an intergration of the breath component from the lungs as well as from the other respiratory organs. Therefore, the breath flowing at the start of exhalation may also be used for the determination of the measuring instant. The introduction of the exhaled breath into the test chamber, i.e., the sample for the alcohol measuring instrument, takes place when the thermal capacity C has been cooled by the temperature $\Delta T$.

The cooling depends on the total volume of air passed by, and on the time span in which it passed by. The condition for the sample taking instant is met, therefore, either by a large volume exhaled in a short time, or by a small volume exhaled in a longer time. In both cases, reliable alcohol test values are obtained. The individual differences in the different test persons thus do not affect the test result.

All it takes for the determination of the measuring instant is to find the temperature difference $\Delta T$ at the thermal capacity C. Complicated volume measurements of the exhaled air and/or flow measurements, possibley relative to the measuring times, in addition, are unnecessary. Extreme environmental conditions can be compensated for in simple manner by also heating the thermal capacity C during the sample taking.

A simple construction or device may be used to carry out the method. All that is needed is the thermal capacity C. It consists of dependable components which present no problems with respect to possible readjustments either. Due to the only determining structural component of the thermal capacity C, a correspondingly simple and, therefore, altogether advantageous arrangement of the other elements, particularly of the electrical components, results.

The arrangement guarantees exact sample taking. Above all, the test person cannot feign a lower alcohol concentration in his exhaled breath by interrupting the exhalation.

The predetermined temperature change $\Delta T$ caused by the flow is obtained through a dissipated amount of heat Q proportional thereto. Both are a function of the duration of the gas flow and its flow rate V. Thus, in a cylindrical part, the cooling $(dQ/dt)$ is proportional to the root of the gas flow rate. When a fixed temperature change $\Delta T$ is specified at the thermal capacity C, it follows from the above root function that this sample taking condition is equivalent in first approximation to the condition that the product of the volume exhaled up to the sample taking and the time required therefor be constant. This means that if a test person exhales briefly, he must exhale a correspondingly greater volume to meet the cooling condition, and vice versa.

When carrying the concept out technically, the circumstance can be taken into account that, after disconnecting the heating power $P_0$ which brings the thermal capacity C to the initial temperature $T_0$, a possibly undesirable natural cooling without gas flow also takes place. If this natural cooling is to be prevented, the heating power $P_0$ may also contine to be supplied to the thermal capacity C after the start of exhalation.

Accordingly, it is an object of the present invention to provide a device for testing a person's breath for determining its alcohol content which comprises a tube through which the person's breath is directed, with a thermal capacitor in the tube including means for heating the capacitor to a predetermined temperature, and further including means for sensing the temperature of the capacitor, the capacitor being coolable after it is heated by the passing of the person's breath thereover so that it is cooled by a predetermined amount comparable to a predetermined change of temperature which has been determined to be a good testing instant, further including means defining a test chamber connected to the tube and control means connected to the sensing means for directing the breathing air from the tube to the test chamber for testing in the test chamber after the predetermined temperature change takes place.

A further object of the invention is to provide a method of testing a person's breath for the determination of its alcohol content in which the measuring instrument for the testing of the person's breath is first determined using a test chamber having means for indicating a particular gas content of the breathing air and a breathing tube through which the breathing air is directed, with a capacitor in the breathing tube which comprises heating the capacitor to a predetermined temperature, cooling the capacitor by directing breathing air over the capacitor and, after the capacitor is cooled by a predetermined amount, directing the breathing air into the test chamber so that it may be tested therein.

A further object of the invention is to provide an apparatus for testing the alcohol content in a person's breath which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
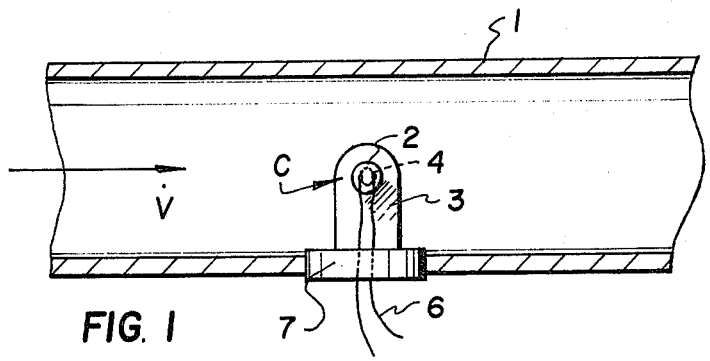
FIG. 1 is a partial sectional view showing a breathing tube having a capacitor therein constructed in accordance with the invention.
Figure 2:
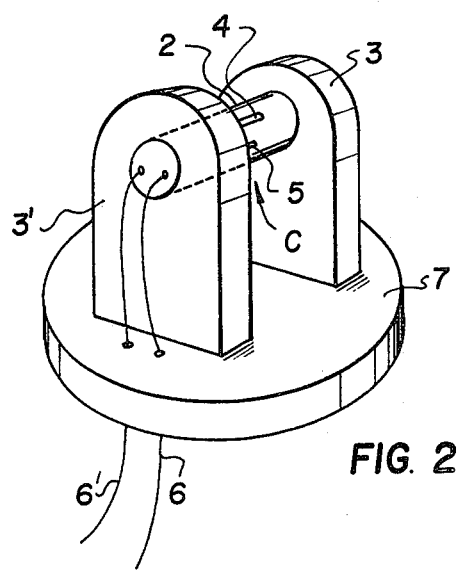
FIG. 2 is an enlarged perspective view of the capacitor shown in FIG. 1.

Referring to the drawings in particular, the invention embodied therein in FIGS. 1 and 2, comprises, a breathing tube 1, through which a person's breath is directed in the direction of the arrow V and which contains a capacitor 2 which may first be heated. The passage of the breathing air over the capacitor 2 cools it down and its change in temperature is used to measure the condition of the breath which makes it most suitable for testing, particularly for determining its alcohol content. When this is determined, as shown in FIG. 3, a valve 20 is actuated to divert the breathing air into a test chamber 50 which contains suitable means for indicating its alcohol content.

As essential component in the consideration of the invention is the thermal capacity component C disposed in the exhaled breath flow. The component C is constituted as a metallic part 2 of cylindrical shape mounted between two brackets 3 and 3' which support it and it is located in the tube 1 carrying the breath of a person being tested. By means of known techniques, part 2 accommodates a heater, e.g., resistance wire or transistor 4, and a temperature sensor 5, for example a thermistor, insulated electrically, but having good mutual thermal contact. The appropriate electrical leads 6 and 6' are insulated and as thin as possible to reduce heat dissipation. The brackets 3 are part of a baseplate 7 and, together, form one injection molded part.

Figure 3:
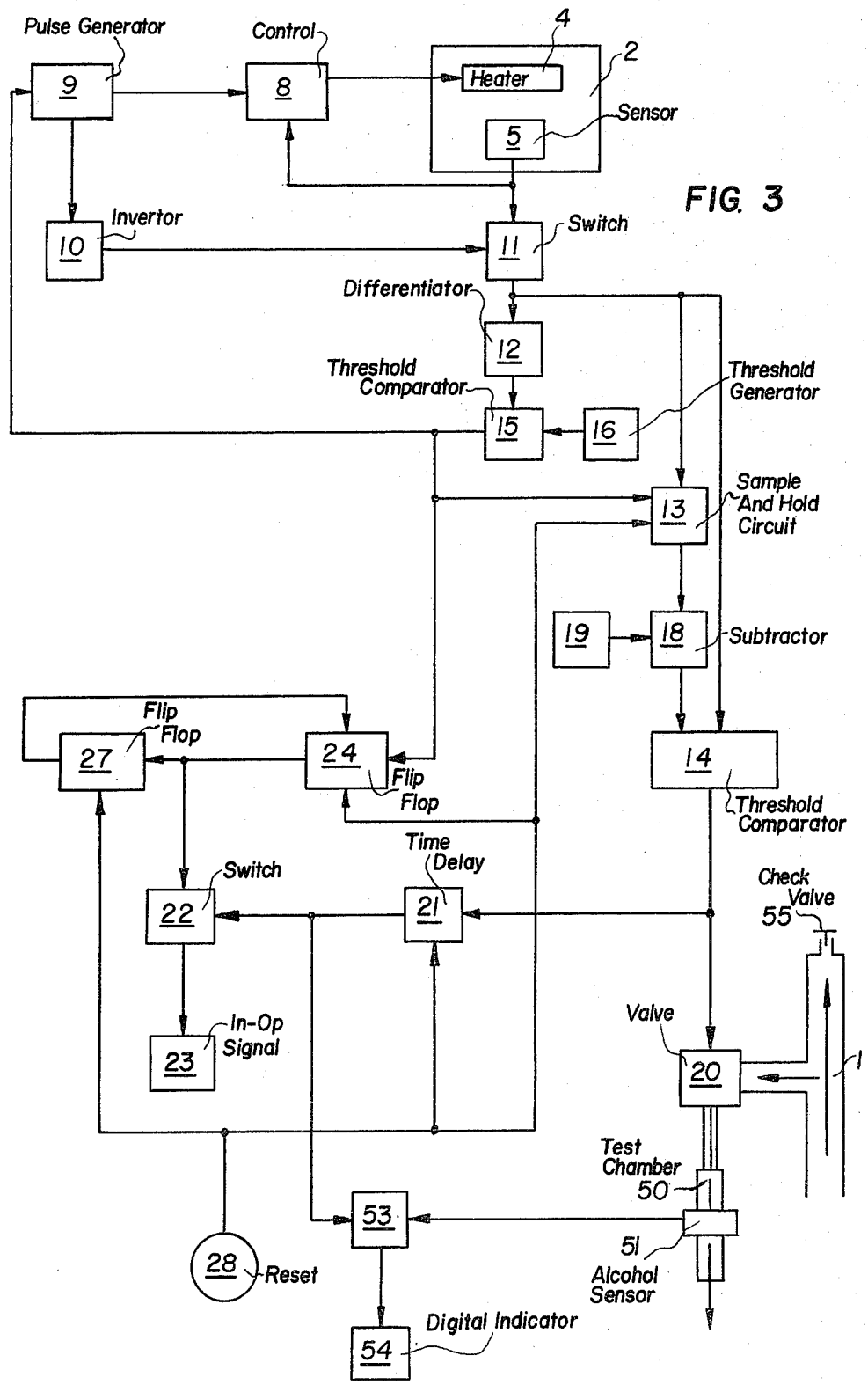
FIG. 3 is a schematic diagram of the electrical controls for determining the desirable testing moment and for testing the breath for its alcohol content in accordance with the present invention.

The electrical circuit wiring for the capacitor system is evident from FIG. 3. A temperature control 8 regulates the heater 4 to the initial temperature $T_0$ of, for example, 120° C., which is measured by the temperature sensor 5. The control is pulse-driven by the pulse generator 9 which drives the control in a 1:1 clock ratio with pulses of 0.25 sec. duration. Another output of the pulse generator is inverted by the inverter 10 and controls the switch 11. Consequently, the switch 11 transmits the temperature signal from 5 only when no pulse driving the control unit is applied to it. The output of the switch 11 is connected to a differentiator 12, a sample and hold circuit 13, and a threshold comparator 14.

The differentiated temperature signal from 12 is fed to a threshold comparator 15 having a threshold generator 16. The cooling of the metallic part 2 from pulse to pulse is (dT/dt) with dT=temperature change, and dt=pulse spacing. If (dT/dt) is above the threshold put in by the threshold generator 16, the threshold comparator 15 furnishes a positive voltage which is applied to the pulse generator 9, stopping it as soon as the threshold comparator 15 has shut off. This also takes the temperature control 8 out of operation and keeps the switch 11 open constantly. Thus, after the test person has started to exhale and a certain cooling rate $R>R_0$, $R_0$=natural cooling without breath flow has been reached, the instrument automatically recognizes the start of the test and shuts off the heater of the part to be cooled.

At the same time, the output of the threshold comparator 15 drives the sample and hold circuit 13 which stores the temperature $T_1$ of part 2 which happened to prevail at the start of the test.

This storage may become necessary because the abovedescribed circuit is capable of fixing the start of the test with a delay of only about 2 pulse lengths, i.e., 0.5 sec, and the temperature may have already dropped somewhat up to then. The temperature difference $\Delta T$, set at the generator 19 and determining the measuring instant, is subtracted in the subtractor 18 from the temperature stored in the sample and hold circuit 13, and the result supplied to one input of the threshold comparator 14. The actual temperature T(t) at part 2 is applied to the other input of the threshold comparator 14. As soon as T(t) becomes smaller than $T_1-\Delta T$, the output signal of the threshold comparator 14 drives the valve 20 and the time delay element 21. The valve 20 introduces the test person's breath gas flow from the tube 1 carrying the breath gas into the test chamber 50 with the alcohol sensor 51.

In case the threshold for (dT/dt) has fallen below at the threshold comparator 15 before the threshold condition is met at the threshold comparator 14, or before the time delay element 21 has a closed switch 22 and an opened switch 53 after the threshold condition of the threshold comparator 14 was met, an "in-op" signal 23 is displayed or, alternatively, a digital measured value indicator 54 for the alcohol concentration blinks. The "in-op" signal is triggered by a flip-flop 24 which switches when a negative flank of the logic output signal from the threshold comparator 15 is applied to it.

Wiring the flip-flop 24 to the flip-flop 27 prevents an erasure of the "in-op" display if (dT/dt), alternating repeatedly, is below or above the threshold given by the threshold generator 16. It is only upon actuation of the reset key 28 that all flip-flops, the sample and hold circuit 13, and the time delay element 21 are returned to their starting positions to ready the instrument for a new test person. The time delay element 21 first has the task of permitting a display at the measured value indicator 54 only when enough time to flush a test chamber 50 has elapsed, and second, to block the "in-op" display from then on so it will not light up when the test person stops exhaling after the end of the test. A check valve 55 in tube 1 prevents inhalation through the instrument.

While a specific embodiment of the invention has been shown and described in detail to illustrate the application of the principles of the invention, it will be understood that the invention may be embodied otherwise without departing from such principles.

What is claimed is:

1. A method of determining the instant of time at which a test for alcohol content in exhaled breath should be initiated comprising:

(a) heating a thermal capacitor having a known thermal capacity $C_o$ to an initial temperature $T_o$;

(b) sensing the temperature of the thermal capacitor;

(c) causing exhaled breath which is to be tested for alcohol content to flow past the thermal capacitor;

(d) stopping the heating of the thermal capacitor when the exhaled breath causes said capacitor to be cooled by a rate greater than that due to natural cooling;

(e) measuring the change in temperature of the thermal capacitor, which change in temperature is indicative of a cooling of the thermal capacitor due to natural cooling plus cooling due to the passing exhaled breath for a period of time, using the sensed temperature of the thermal capacitor;

(f) comparing the change in temperature of step (e) with a known change in temperature for the thermal capacitor which corresponds to cooling by a sufficient total volume of exhaled breath past the thermal capacitor j; and (g) determining the instant of time at which the measured change in temperature at least equals the known change in temperature, which instant substantially equals the instant of time at which the test for alcohol content should be initiated.

2. A method according to claim 1, wherein the step of stopping further comprises;

sensing the temperature of the thermal capacitor at regular intervals of time;

determining a value $dT/dt$ corresponding to a change in temperature of the thermal capacitor per each interval of time;

comparing the determined value of $dT/dt$ to a known value for a natural cooling $R_o$ for the thermal capacitor with no exhaled breath passing; and stopping the heating of the thermal capacitor when $dT/dt$ at least equals $R_o$, which is indicative of a cooling of the thermal capacitor due to passing exhaled breath.

3. A method according to claim 1, wherein said thermal capacitor is metallic and cylindrical and has a cooling rate $dQ/dt$ which is approximately equal to the square root of the exhausted breath flow rate.

4. A method according to claim 1, further including:

directing exhaled breath which has passed the thermal capacitor to the alcohol test chamber only after said instant of time.

5. A device for determining an instant of time for testing a person's breath for its alcohol content, comprising, a tube through which the person's breath is directed, a thermal capacitor having known thermal capacity in said tube including means for heating said capacitor to a predetermined initial temperature, means for sensing the temperature of said capacitor, said capacitor being adapted to be cooled by a person's breath passing through the tube, comparator means for determining the instant of time when said capacitor is cooled by a predetermined amount, means defining a test chamber connected to said tube, and value means controlled by said comparator means for directing the breathing air from said tube to said test chamber for testing therein after said instant, and control means for stopping said heating means when breath first passes said thermal capacitor.

6. A device according to claim 5, wherein said thermal capacitor comprises a cylindrical metallic body, said means for heating said capacitor comprises a heating element in said body and said means for sensing the temperature of said capacitor comprises a temperature sensor in said body.

7. A device as claimed in claim 5, wherein said device includes a support located in said breathing tube; first and second spaced apart brackets mounted on said support; and said capacitor comprises a cylindrical metallic body adapted to be supported by said brackets, wherein said means for heating comprises an electrical heater element disposed in said cylindrical metallic body for heating said body.

8. A device as claimed in claim 7, wherein said metallic body is of a shape so that its cooling rate $(dQ/dt)$ is a root function of a gas flow rate V such that $$\frac{dQ}{dt} \sim \sqrt{V}.$$

* * * * *